United States Patent [19]

Terada

[11] 3,960,143

[45] June 1, 1976

[54] ENDOSCOPE WITH A TUBE FOR A MEDICAL TREATING INSTRUMENT

[75] Inventor: Masaaki Terada, Tokyo, Japan

[73] Assignee: Olympus Optical Co., Ltd., Tokyo, Japan

[22] Filed: Aug. 26, 1974

[21] Appl. No.: 500,612

[30] Foreign Application Priority Data

Aug. 31, 1973   Japan...................... 48-102346[U]

[52] U.S. Cl. .................................................. 128/4
[51] Int. Cl.$^2$.......................................... A61B 1/00
[58] Field of Search .............................. 128/4–11, 128/303.15, 303.17

[56] References Cited
UNITED STATES PATENTS 3,144,020   8/1964   Zingale ................................. 128/4
3,561,432   2/1971   Yamaki et al. ......................... 128/6
3,670,721   6/1972   Fukama et al. ......................... 128/6

FOREIGN PATENTS OR APPLICATIONS 1,347,596   11/1963   France .................................. 128/4

Primary Examiner—Robert W. Michell
Assistant Examiner—Henry S. Layton

[57] ABSTRACT

An endoscope is equipped with a tube consisting of at least two layers and having a passage through which forceps or catheter is inserted. One layer constituting an inner layer is made of a relatively rigid material whose frictional coefficient is small. The other layer constituting an outer layer is made of a flexible or pliable material and is thicker than the inner layer.

2 Claims, 4 Drawing Figures

ENDOSCOPE WITH A TUBE FOR A MEDICAL TREATING INSTRUMENT

BACKGROUND OF THE INVENTION

This invention relates to an endoscope and more particularly to a tube for inserting a medical treating instrument such as a forceps and catheter toward a human body cavity.

Generally, a human body cavity is intricately meandered or abruptly turned. When an endoscope is inserted into the body cavity, if a flexible tube is less pliable, there is a fear that the inner wall of the body cavity will be injured, giving pains to a patient. The flexibility of the flexible tube is varied dependent upon the material of the flexible tube, as well as a tube for inserting a medical treating instrument such as forceps and catheter toward the body cavity, image or light guiding fiber bundles etc. all of which are disposed within the flexible tube. However, the image or light guiding fiber bundles are made of a relatively flexible or pliable material. Consequently, the flexibility of the flexible tube is largely dependent upon the tube through which the medical treating instrument is inserted.

A conventional tube for inserting a medical treating instrument toward a body cavity is made of a flexible material and constitutes a single-layer wall, not a multi-layer wall. Some is satisfactory with respect to flexibility or pliability. However, when forceps is inserted through a flexible tube into a sinuous body canal, there are the cases where the tip portion of the forceps abuts against, and bits into, the inner wall of the tube with the result that any further insertion is almost impossible. If at this time the forceps is further forced into the tube, the tube per se is greatly moved within a flexible tube with the resultant injury to the other adjacent members, such as fiber bundles and suction tube disposed within the flexible tube. Furthermore, a lot of time is spent if the instrument is not smoothly inserted through the tube. In some case, the forceps does not extend from the distal end section of the endoscope, making it impossible to observe or examine the body cavity of the patient.

If the tube is made of a relatively rigid material, the inner surface of the tube can be made slippery. However, this advantage is offset by the disadvantage that the flexibility of the tube is sacrificed.

SUMMARY OF THE INVENTION

The feature of this invention resides in an endoscope equipped with a tube having a passage through which a medical instrument is inserted, said tube consists of at least two layers, one layer constituting a thin inner layer being made of a hard surfaced material whose frictional coefficient is small and the other layer constituting an outer layer being made of a flexible or pliable material.

According to this invention, the inner surface of the tube admits of easy slidable engagement with an instrument. It is therefore possible to smoothly insert the instrument through the tube. Since the inner layer of the tube is made thin, the tube as a whole still retains flexibility. If in this case the tube is formed by the thin inner layer alone, it is considered possible to smoothly insert the instrument through the tube without losing the flexibility of the tube. In actual practice, however, the tube tends to collapse if a flexible tube is guided along the bent canal of the human body. As a result, any further insertion is almost impossible. With the tube according to this invention, any collapse of the tube is prevented, since the outer layer is made of the flexible material. In one aspect of this invention, the outer layer as a whole has a thickness equal to 2-5 times the thickness of the inner layer.

An object of this invention is to provide a tube for smoothly inserting a medical instrument such as forceps to a human body cavity without losing the flexibility of the tube.

The other object of this invention will be understood by reference to the explanation of preferred embodiments and the disclosure of the accompanying drawings.

DESCRIPTION OF THE PREFERRED EMBODIMENTS

Figure 1:
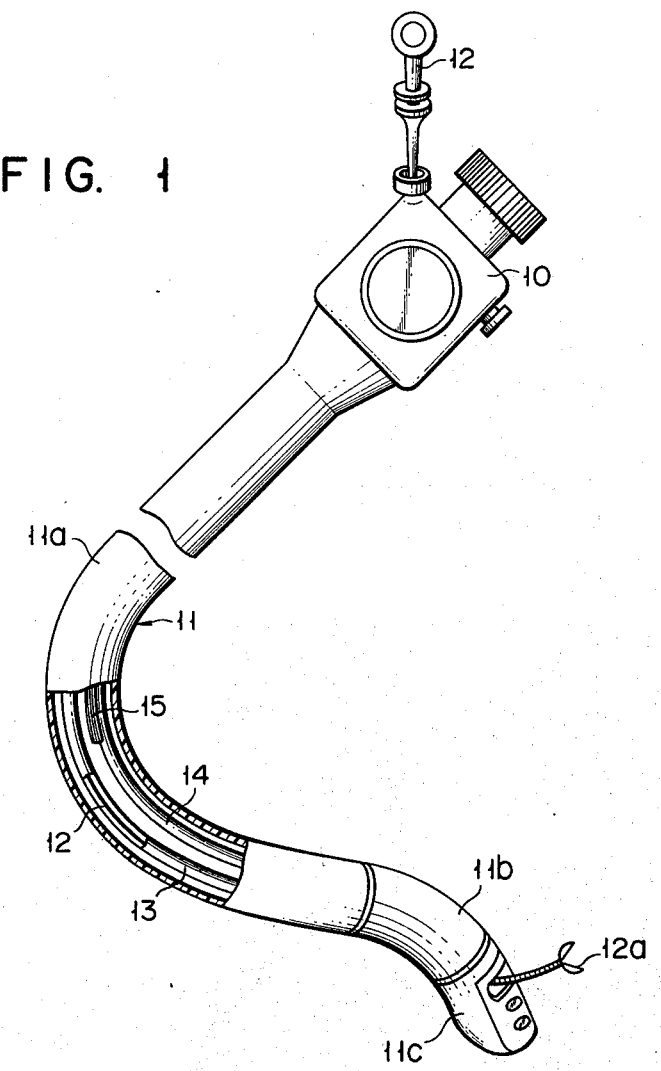
FIG. 1 is a view, partially broken away, showing the general construction of an endoscope.

FIG. 1 shows the general construction of an endoscope. The endoscope comprises a control unit 10 and a flexible tube 11. The flexible tube 11 consists of a main flexible section 11a, a bending section 11b and a distal end section 11c. Within the flexible tube 11 are disposed a tube 13 for sending a lengthy medical treating instrument such as biopsy forceps 12, catheter etc. to a body cavity, a suction tube 14, a fiber bundle 15 etc. The flexible tube 11 is adapted to be inserted into the body cavity of a patient so that the inner surface of the body cavity can be observed or examined. Forceps 12 is inserted from the control unit 10 into the tube 13 and extends into the body cavity of the patient.

Figure 2:
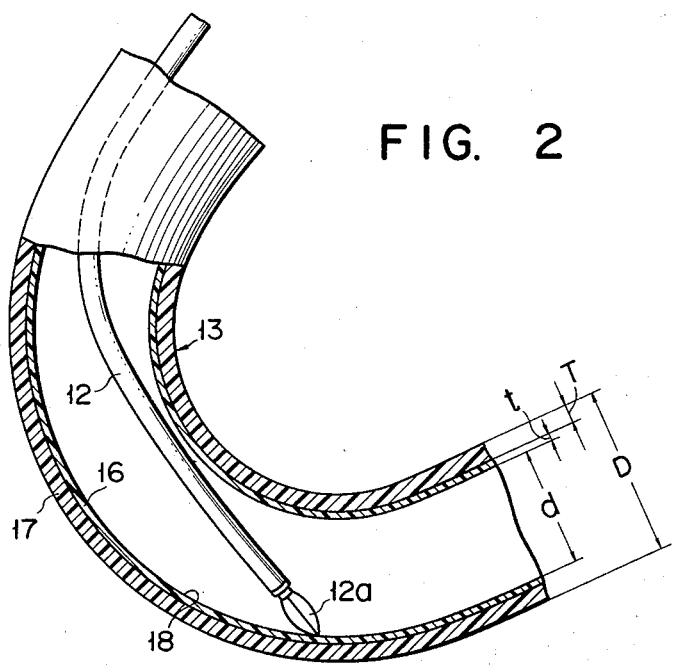
FIG. 2 is an enlarged, fragmentary view showing a tube according to a first embodiment of this invention in which forceps is inserted.

FIG. 2 is a fragmentary cross-sectional view of the tube 13. The tube 13 has a double-layer wall. The inner layer 16 is made of a material whose frictional coefficient is small and is thin, but relatively rigid in nature, while the outer layer 17 is made of a flexible or pliable material and is thicker than the inner layer 16. Both the layers 16 and 17 are mechanically or thermally bonded together. Alternatively, the double-layer wall of the tube 13 can be simultaneously extrusion molded.

As a material for the inner layer 16, cross-linked polyethylene and polytetrafluoroethylene commercially available under the trade name of Teflon are suitable. As a material for the outer layer 17, synthetic rubber and cross-linked polyethylene blended with vinyl acetate are suitable.

A double-layer wall of the tube 13 having an inner diameter $d$ of 4 mm and an outer diameter $D$ of 6 mm with the inner layer 16 having the thickness $t$ of 0.2 mm and the outer layer 17 the thickness $T$ of 0.8 mm was used in actual practice. As will be evident from these data, the outer layer 17 of the tube 13 is four times as thick as the inner layer 16. The flexibility of the tube 13 as a whole is mainly dependent upon the material of the outer layer 17. Since, however, the outer layer 17 is made of the flexible material, the tube 13 has a high flexibility as a whole.

When the forceps 12 is inserted into a passage 18 of the tube 13, if the tube 13 is rather sharply bent as shown in FIG. 2, the foreceps 12 abuts against the inner surface of the tube 13. Since, however, the inner layer 16 of the tube 13 is made of the relatively rigid material whose frictional coefficient is small, the tip portion 12a of the forceps 12 slides along the inner surface of the tube 13 without leaving any injury and is smoothly guided along the inner surface of the tube 13 toward the body cavity.

Though with the above-mentioned embodiment the outer layer 17 is four times as thick as the inner layer 16, it may be 2–5 times as thick as the inner layer 16.

Figure 3:
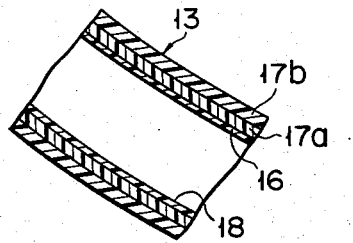
FIG. 3 is an enlarged, fragmentary view showing a second embodiment according to this invention.

FIG. 3 shows a tube 13 according to a second embodiment of this invention. The tube 13 has a 3-layer wall. An inner layer 16 is made of a relatively rigid material whose frictional coefficient is small. For example, polytetrafluoroethylene and cross-linked polyethylene are used as the material for the inner layer 16. The other outer layers 17a and 17b are disposed around the inner layer 16 and each made of a flexible material such as synthetic rubber and cross-linked polyethylene blended with vinyl acetate. The outer layers 17a and 17b are each thicker than the inner layer 16. The sum of the thickness of the outer layer 17a and the thickness of the outer layer 17b is equal to about 5 times the thickness of the inner layer 16. In this way, the tube 13 constitutes a multi-layer tube having at least two layers.

Figure 4:
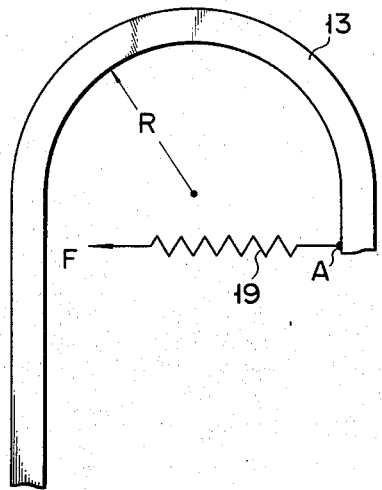
FIG. 4 shows the manner in which the flexibility of the tube is determined.

The flexibility of the tube was determined as follows:

As shown in FIG. 4, one end of a spring balance 19 was attached at one spot A of the outer surface of the tube 13 and then the tube was so bent that the curvature radius R is made equal to 25 mm. At this time, the magnitude of the spring force F of the spring balance 19 was determined. In the 2-layer tube 13 according to the first embodiment of this invention, when $d = 4$ mm, $D = 6$ mm, $t = 0.2$ mm and $T = 0.8$ mm, the spring force F was found to be 300g. From this it will be understood that the tube 13 is never inferior in flexibility to a conventional single-layer tube heretofore used.

Determinations were also made under the identical conditions:

1. except that the outer layer 17 is made of the same rigid material as the inner layer 16.
2. except that the inner layer 16 is made of the same flexible material as the outer layer 17.

In the former case (1), the spring force F was found to be 600g, while in the latter case (2) the spring force F was found to be 225g.

According to this invention, synthetic rubber and plastics such as cross-linked polyethylene are used for the inner and outer layers of the tube 13. Since, in this case, the extent of flexibility corresponds to the extent of hardness, the flexibility test can also include a hardness test.

As mentioned above, the multi-layer tube according to this invention permits a medical treating instrument such as forceps, catheter etc. to be easily guided therethrough, since the inner layer is hard surfaced and admits of easy slidable engagement with the instrument. Therefore, there is no fear that the tip portion of the treating instrument will bite into the inner wall of the tube 13. As a result, there is prevented any injury to the other members disposed adjacent to the tube 13. Though the outer layer is thicker than the inner layer, it still retains pliability or flexibility, since it is made of the flexible material. Consequently, the flexible tube 11 can be inserted into the body cavity of the patient without losing its pliability or flexibility and any pain given to the patient during insertion is alleviated.

What is claimed is:

1. In a tube disposed in a flexible sheath of an endoscope together with a fiber bundle, a suction tube adapted to receive therethrough a medical treating instrument including a biopsy forceps and a catheter, the improvement comprising constructing said tube of at least two layers superposed one upon the other, one of said layers being an inner layer made of a hard surfaced material having an inner surface of a small frictional coefficient, and the other layer being an outer layer made of a flexible material and thicker than said inner layer, thick enough to prevent the collapse of the inner layer, and as a whole having a thickness equal to 2–5 times the thickness of said inner layer.

2. In a tube disposed in a flexible sheath of an endoscope together with a fiber bundle, a suction tube adapted to receive therethrough a medical treating instrument including a biopsy forceps and a catheter, the improvement comprising constructing said tube of at least two layers superposed one upon the other, one of said layers being an inner layer made of a hard surfaced material, having an inner surface of a small frictional coefficient, and being selected from the group consisting of cross-linked polyetheylene and polytetrafluoroetheylene, the other layer being an outer layer made of a flexible material and thicker than said inner layer, thick enough to prevent the collapse of the inner layer, said outer layer being made of one material selected from the group consisting of synthetic rubber and cross-linked polyethylene blended with vinyl acetate.

* * * * *